(12) United States Patent
Hardy et al.

(10) Patent No.: US 9,782,514 B2
(45) Date of Patent: Oct. 10, 2017

(54) FILM FORMING COMPOSITON

(75) Inventors: Craig Julian Hardy, Cheshire (GB); Andrew Darby, Staffs (GB)

(73) Assignee: MED-TRADE PRODUCTS LIMITED, Crewe Business Park Crewe, Cheshire (GB)

( * ) Notice: Subject to any disclaimer, the term of this patent is extended or adjusted under 35 U.S.C. 154(b) by 1587 days.

(21) Appl. No.: 11/914,143

(22) PCT Filed: May 11, 2006

(86) PCT No.: PCT/GB2006/001734
§ 371 (c)(1),
(2), (4) Date: May 7, 2008

(87) PCT Pub. No.: WO2006/120454
PCT Pub. Date: Nov. 16, 2006

(65) Prior Publication Data
US 2008/0311071 A1    Dec. 18, 2008

(30) Foreign Application Priority Data

May 12, 2005 (GB) .................................. 0509690.4

(51) Int. Cl.
*A61L 26/00* (2006.01)

(52) U.S. Cl.
CPC ....... *A61L 26/0076* (2013.01); *A61L 26/0052* (2013.01)

(58) Field of Classification Search
CPC .. A61L 26/0076; A61L 26/0052; C08L 75/04; A61K 9/006; A61K 9/08; A61K 9/10
See application file for complete search history.

(56) References Cited

U.S. PATENT DOCUMENTS

| 4,486,488 | A | * | 12/1984 | Pietsch et al. | ................. | 602/60 |
| 4,780,512 | A | * | 10/1988 | Gould et al. | ................. | 525/454 |
| 5,041,287 | A | * | 8/1991 | Driggers | ............... | A61B 19/04 424/47 |
| 5,792,469 | A | * | 8/1998 | Tipton et al. | ................. | 424/422 |
| 5,856,248 | A | * | 1/1999 | Weinberg | ..................... | 442/118 |
| 2005/0079147 | A1 | * | 4/2005 | Delaey et al. | ............. | 424/78.08 |

FOREIGN PATENT DOCUMENTS

| EP | 0065370 A1 | * | 11/1982 |
| GB | 2150938 A | | 7/1985 |
| GB | 2222173 A | | 2/1990 |
| WO | 0010540 | | 3/2000 |

OTHER PUBLICATIONS

Noveon, Inc., "Avalure Film forming Polymers for Personal Care Applications", Edition: Feb. 10, 2006, 2006.

* cited by examiner

*Primary Examiner* — Lakshmi Channavajjala
(74) *Attorney, Agent, or Firm* — Barlow, Josephs & Holmes, Ltd.

(57) ABSTRACT

The present application relates to a film forming composition for application to mammalian skin, which composition comprises at least one polyurethane based polymer together with at least one acrylate based polymer. The film forming composition provides effective skin coating with good adhesion to the skin, and may be used as a skin protector or a wound dressing.

23 Claims, No Drawings

FILM FORMING COMPOSITON

The present invention relates to a protective film composition which finds particular utility in forming a film over mammalian skin.

Existing films suitable for application to the skin are based on cyanoacrylate chemistry as is commonly used in superglue. Unsurprisingly, these films share many of the characteristics of superglue, in particular they actually stick skin together. Clearly this is undesirable for a product intended to be used on the skin. Moreover, extreme care is required during its application to the skin. The product also has limited applications in terms of the areas to which it can be applied. The product also tends to require an applicator and in some cases further mixing with chemicals is required. Furthermore, once exposed to air, these products tend to "go off" very rapidly and as such have a short lifespan.

Other non-cyanoacrylate based products include Cavilon® which is based on a silicone polymer and Nu-Skin® which is a nitrocellulose based compound comprising ethyl acetate and ethanol.

Although Cavilone® provides a water-proofing effect it is difficult to apply effectively as the user cannot be sure that a complete coat has been achieved. Furthermore, Cavilon® is a particularly expensive product.

As Nu-Skin® is nitrocellulose based it has a disagreeable odour. Furthermore, the product is unsuitable for application to open wounds as it causes the wound to sting. The product gives rise to a heavy coating which tends to crack and flake within one or two hours of application. Therefore, the product is uncomfortable to 'wear' and as frequent reapplication is necessary it is uneconomical.

In addition to the foregoing products there are several generic products available which use a silicone fluid. These products are essentially waterproofing barrier creams/lotions. However, the products do not form a film upon the skin and as such tend to wash/wear off within 24 or 48 hours.

Therefore, it is desirable to provide a composition which forms a film upon mammalian skin which in doing so provides a long lasting waterproofing effect and yet which is mild enough to be applied to open wounds without causing stinging.

According to the first aspect of the present invention there is provided a film forming composition for application to mammalian skin or a breach in the skin comprising at least one polyurethane based polymer together with at least one acrylate based polymer.

Advantageously, the composition of the present invention is in liquid form thus facilitating its application to the skin. It provides an effective skin coating with good adhesion to the skin. Furthermore, the composition is preferably clearly visible once applied in order to assist application and ensure that a desired area is completely covered. Application of the composition does not require a separate applicator.

The composition may also be safely applied to breaches in the skin, such as wounds. Advantageously, the composition can be applied to an open wound without causing stinging. Moreover, if the wound has exposed nerve endings the protective film quickly seals the wound such that a reduction in pain is observed.

The composition of the present invention is easy to apply and does not stick skin together.

Therefore, the composition of the present invention can be used as a skin protector on intact skin or as a wound dressing for application directly onto a wound.

Thus, according to a second aspect of the present invention there is provided a polymeric protective film obtainable by applying to mammalian skin or a breach in the skin a film forming composition comprising at least one polyurethane based polymer together with at least one acrylate based polymer.

The film forming composition may typically be applied to the skin or a breach in the skin in the form of a liquid, cream, emulsion, gel or paste. The composition dries in situ to form a protective film. The composition may dry to form a protective skin within around 10 minutes or less. In some embodiments, the drying time may be around 5 minutes or less, and in some embodiments drying of the composition may take around 3 minutes or less.

According to a further aspect of the present invention there is provided the use of a film forming composition comprising at least one polyurethane based polymer together with at least one acrylate based polymer as a skin protector.

According to a still further aspect of the present invention there is provided the use of a film forming composition comprising at least one polyurethane based polymer together with at least one acrylate based polymer as a wound dressing.

Said polyurethane based polymer comprises a polyurethane or polyurethane derivative. Said polyurethane based polymer may be in the form of an emulsion, a fluid suspension, a solution or any combination thereof.

Polyurethane based polymers suitable for use with the present invention include any of the following either alone or in combination: polyurethane, polyetherpolyurethane, polyureapolyurethane, copolymers of polyurethane, polyurethane/silicone copolymers, polyurethane/acrylic copolymers, polyurethane adhesives, polyurethane derivatives, polyurethane elastomers, polyurethane prepolymers, polyurethane hydrogels.

It is to be understood that the foregoing examples are provided by way of example only and the invention is not intended to be limited thereby.

Said polyurethane based polymer may constitute from 0.1% to 99.9% w/w, preferably from 0.5% to 99.5% w/w, more preferably from 2.5% to 97% w/w, still more preferably from 10% to 90% w/w and most preferably from 50% to 75% w/w of the total composition.

Said acrylate based polymer comprises any suitable acrylate or acrylic derivative. Said acrylate based polymer may be in the form of an emulsion, a fluid suspension, a solution or any combination thereof.

Acrylic based polymers suitable for use with the present invention include any of the following either alone or in combination: polyacrylic acid, carbomer, carboxyvinyl polymer, carboxypolymethylene polymer, polyacrylate elastomers, polyacrylates, polyacrylate copolymer, polyacrylate crosspolymers, acrylates/alkyl acrylate crosspolymer, AMP-acrylates/Allyl Methacrylate Copolymer, acrylates/acrylamide copolymer, acrylic acid/alkyl methacrylate copolymer, silicone/acrylates copolymer, acrylates/polyurethane copolymer.

It is to be understood that the foregoing examples are provided by way of example only and the invention is not intended to be limited thereby.

Said acrylate based polymer may constitute from 0.1% to 99.9% w/w, preferably from 0.5% to 99.5% w/w, more preferably from 2.5% to 97% w/w, still more preferably from 10% to 90% w/w and most preferably from 25% to 50% w/w of the total composition.

The composition of the present invention may also comprise any of the following either alone or in combination: viscosity enhancing compounds including but not limited to carbomers and viscosity enhancing salts, such as sodium chloride and similar salts; polyols; solvents; volatile solvents; antimicrobials including but not limited to silver salts, silver complexes, chlorhexidine, benzalkonium halides; agents for adversely affecting biofilms; adhesives; preservatives; waterproofing agents; growth factors; healing agents; surfactants; moisturisers; herbal extracts, amino acids, pH altering compounds; cleansers; haemostats; other skin adhesives; and other film forming compounds.

In preferred embodiments, water is used as a solvent. Advantageously, this avoids the use of solvents which can cause stinging or pain when applied to a wound or other breach in the skin.

Surprisingly, the composition of the present invention has been found to be resistant to gamma sterilisation, in that the viscosity of the composition is not significantly adversely affected by the gamma radiation. In contrast to this, currently available film forming compositions are not resistant to gamma sterilisation and their film forming properties tend to be compromised as a result of their exposure to gamma radiation. Advantageously, gamma irradiation of the compositions according to aspects of the present invention may result in compositions which dry on skin to form more robust films when compared to non-irradiated compositions.

Clearly the ability of the compositions of the present invention to be sterilised renders them suitable for application in a wider range of wounds types and gives access to additional market areas.

Thus, according to a further aspect of the present invention there is provided a method for the preparation of a sterile film forming composition for application to mammalian skin or a breach in the skin comprising the steps of: mixing together a polyurethane based polymer and an acrylate based polymer, and irradiating the resulting mixture using gamma radiation.

According to a further aspect of the present invention there is provided a sterile film forming composition for application to mammalian skin or a breach in the skin, obtainable by mixing together a polyurethane based polymer and an acrylate based polymer, and irradiating the resulting mixture using gamma radiation.

Typically, the composition according to aspects of the present invention is provided as a liquid, cream, emulsion, gel or paste.

It is envisaged that the composition may also be available in the form of a skin wipe. In this embodiment the composition of the present invention is absorbed onto a suitable fibrous material such as a cellulose material.

It is also envisaged that the composition may be in the form of a spray.

The present invention will now be described further by way of example only and with reference to the following examples:

EXAMPLE 1

| Material | Description | Concentration |
| --- | --- | --- |
| Avalure AC 118 | Acrylic based polymer in solution | 50% |
| Avulure UR 425 | Polyurethane based polymer in solution | 50% |

The two components are mixed together at room temperature using a stirrer for 15 minutes. The resulting white liquid can be easily spread on to skin and dries to give a uniform visible film barrier.

The film barrier adheres well to the skin and remains intact and in place for over 24 hours protecting the skin from external factors.

EXAMPLES 2 TO 5

| Components | Example 2 | Example 3 | Example 4 | Example 5 |
| --- | --- | --- | --- | --- |
| Avalure AC 118 | 100% | 0% | 25% | 25% |
| Avulure UR 425 | 0% | 100% | 50% | 50% |
| Water | None | None | 25% | 25% |
| Sterilised? | No | No | No | Yes. Gamma 25 kgry |
| Drying Time | 2 mins | 2.5 mins | 4 mins | 4 mins |
| Film format | Does not form a discrete coating on the skins surface. Can not be removed or peeled off. | Forms a discrete film, but the film is weak and adherence to the skin is also weak. | Forms a discrete robust film with good adherence to the skin | Forms a discrete robust film with good adherence to the skin |
| Wear time or exposed film. | Coating offers no protect from moist external factors. | Film begins to fall off almost immediately. | 24 hours before any cracking. Main bulk of the film last for a further 2 days. | 24 hours before any cracking. Main bulk of the film last for a further 3 days. |
| Adhesion of dressing to film/skin | Good | Good but film lift easily off skin and dressing falls off | Good | Good |

EXAMPLES 6 TO 9

| Components | Example 6 | Example 7 | Example 8 | Example 9 |
|---|---|---|---|---|
| Avalure AC 120 | 33.3% | 25% | 25% | 25% |
| Avulure UR 425 | 67.7% | 50% | 50% | 50% |
| Water | None | 24.7% | 25% | 24.8% |
| Carbomer | None | 0.3% | None | None |
| Silver Nitrate | None | None | None | 0.2% |
| Sterilised? | No | Yes. Gamma 25 kgry | Yes. Gamma 25 kgry | No |
| Drying Time | 2 mins | 3.5 mins | 4 mins | 4 mins |
| Film format | Forms a discrete robust film with good adherence to the skin. | Forms a discrete robust film with good adherence to the skin. | Forms a discrete robust film with good adherence to the skin | Forms a discrete slightly coloured robust film with good adherence to the skin |
| Wear time or exposed film. | 24 hours before any cracking. Main bulk of the film last for a further 2 days. | 24 hours before any cracking. Main bulk of the film last for a further 2 days. | 24 hours before any cracking. Main bulk of the film last for a further 2 days. | 24 hours before any cracking. Main bulk of the film last for a further 3 days. |
| Adhesion of dressing to film/skin | Good | Good | Good | Good |

EXAMPLES 10 TO 13

| Components | Example 10 | Example 11 | Example 12 | Example 13 |
|---|---|---|---|---|
| Avalure AC 120 | 5% | 23% | 49.5% | 49.975% |
| Avulure UR 425 | 95% | 50% | 50% | 50% |
| Water | None | 24.7% | None | None |
| Carbomer | None | 0.3% | None | None |
| Calcium chloride | 0.1% | None | None | |
| Hyaluronic Acid | None | None | None | 0.025% |
| Glycerol | None | 2% | None | None |
| Waterproofing agent (silicone emulsion) | None | None | 0.25% Silicone oil 0.25% Novemer EC-1 | None |
| Sterilised? | Yes Gamma 25 Kgy | Yes. Gamma 25 kgry | No | No |
| Drying Time | 2 mins | 4.5 mins | 3.5 mins | 2.5 mins |
| Film format | Forms a discrete robust film with good adherence to the skin. The film contains calcium ions which are know to have a beneficial effect on the intrinsic blood clotting cascade. | Forms a discrete robust film with good adherence to the skin. The film contains a humectant/moisturiser (glycerol) and is softer and more flexible. | Forms a discrete robust film with good adherence to the skin. | Forms a discrete slightly coloured robust film with good adherence to the skin |
| Wear time or exposed film. | 24 hours before any cracking. Main bulk of the film last for a further 2 days. | 36 hours before any cracking. Main bulk of the film last for a further 1 day. | 24 hours before any cracking. Main bulk of the film last for a further 2 days. | 24 hours before any cracking. Main bulk of the film last for a further 2 days. |
| Adhesion of dressing to film/skin | Good. | Acceptable | Acceptable | Good |

EXAMPLES 14 TO 17

Sodium chloride was dissolved in water. The two polymer components were mixed together at room temperature using a stirrer for 15 minutes, The salt solution was added to the polymer mixture and the combination stirred for 1 hour. The resulting white product can be easily spread on to skin and dries to give a uniform visible film barrier. Product made with above 0.3% sodium chloride showed an increase in viscosity which was apparent to an observer. This viscosity increase developed over a period of a few hours.

The film barrier adheres well to the skin and remains intact and in place for over 24 hours protecting the skin from external factors. The film barrier from product containing over approximately 0.45% sodium chloride is distinctly stronger and more robust.

| Components | Example 14 | Example 15 | Example 16 | Example 17 |
|---|---|---|---|---|
| Avalure AC 118 | 46% | 46% | 46% | 46% |
| Avulure UR 425 | 46% | 46% | 46% | 46% |
| Water | 7.7% | 7.7% | 7.7% | 7.7% |
| Sodium Chloride | 0.3% | 0.45% | 0.6% | 0.9% |
| Sterilised? | No | No | No | No |
| Format | Liquid | Thick liquid | Cream | Semi solid emulsion |
| Drying Time | 3 mins | 3 mins | 3 mins | 3.5 mins |
| Film format | Forms a distinct robust film with good adherence to the skin | Forms a distinct robust film with good adherence to the skin | Forms a distinct very robust film with good adherence to the skin | Forms a discrete very robust film with good adherence to the skin |
| Wear time or exposed film. | 24 hours before any cracking. Main bulk of the film last for a further 2 days. | 24 hours before any cracking. Main bulk of the film last for a further 2 days. | 48 hours before any cracking. Main bulk of the film last for a further 2 days. | 48 hours before any cracking. Main bulk of the film last for a further 3 days. |
| Adhesion of dressing to film/skin | Good | Good | Good | Good |

EXAMPLES 18 TO 21

Sodium chloride was dissolved in the water. The two polymer components were mixed together at room temperature using a stirrer for 15 minutes. The salt solution and glycerol were added to the polymer mixture and the combination stirred for 1 hour. The resulting white product can be easily spread on to skin and dries to give a uniform visible film barrier.

The film barrier adheres well to the skin and remains intact and in place for over 24 hours protecting the skin from external factors. The film barrier from product containing glycerol is distinctly more robust.

| Components | Example 18 | Example 19 | Example 20 | Example 21 |
|---|---|---|---|---|
| Avalure AC 118 | 44% | 44% | 44% | 44% |
| Avulure UR 425 | 44% | 44% | 44% | 44% |
| Water | 7.7% | 7.7% | 7.7% | 7.7% |
| Sodium Chloride | 0.3% | 0.45% | 0.6% | 0.9% |
| Glycerol | 4% | 4% | 4% | 4% |
| Sterilised? | No | No | No | No |
| Format | Liquid | Thick liquid | Cream | Semi solid emulsion |
| Drying Time | 3 mins | 3 mins | 3 mins | 3.5 mins |
| Film format | Forms a distinct robust film with good adherence to the skin | Forms a distinct robust film with good adherence to the skin | Forms a distinct very robust film with good adherence to the skin | Forms a discrete very robust film with good adherence to the skin |

-continued

| Components | Example 18 | Example 19 | Example 20 | Example 21 |
|---|---|---|---|---|
| Wear time or exposed film. | 48 hours before any cracking. Main bulk of the film last for a further day. | 48 hours before any cracking. Main bulk of the film last for a further day. | 72 hours before any cracking. Main bulk of the film last for a further 2 days. | 72 hours before any cracking. Main bulk of the film last for a further 2 days. |
| Adhesion of dressing to film/skin | Good | Good | Good | Good |

EXAMPLES 22 TO 25

Sodium chloride was dissolved in the water. The two polymer components were mixed together at room temperature using a stirrer for 15 minutes. The salt solution was added to the polymer mixture and the combination stirred for 1 hour.

The resulting product was gamma sterilised with a nominal dose of 25 kgry.

The resulting white product can be easily spread on to skin and dries to give a uniform visible film barrier. The gamma sterilised product does not lose viscosity.

The film barrier adheres well to the skin and remains intact and in place for over 24 hours protecting the skin from external factors. The film barrier from gamma sterilised product is distinctly stronger and more robust.

EXAMPLES 26 TO 29

Sodium chloride was dissolved in the water. The two polymer components were mixed together at room temperature using a stirrer for 15 minutes. The salt solution and glycerol were added to the polymer mixture and the combination stirred for 1 hour.

The resulting white product was gamma sterilised with a nominal dose of 25 kgry and showed no loss of viscosity.

The product dries to give a film barrier which adheres well to the skin and remains intact and in place for over 48 hours protecting the skin from external factors. The film barriers from sterilised product containing glycerol are distinctly more robust.

| Components | Example 22 | Example 23 | Example 24 | Example 25 |
|---|---|---|---|---|
| Avalure AC 118 | 46% | 46% | 46% | 46% |
| Avulure UR 425 | 46% | 46% | 46% | 46% |
| Water | 7.7% | 7.7% | 7.7% | 7.7% |
| Sodium Chloride | 0.3% | 0.45% | 0.6% | 0.9% |
| Sterilised? | yes | yes | yes | yes |
| Format before gamma | Liquid | Thick liquid | Cream | Semi solid emulsion |
| Format after gamma | Liquid | Thick liquid | Cream | Semi solid emulsion |
| Drying Time | 3 mins | 3 mins | 3 mins | 3.5 mins |
| Film format | Forms a distinct very robust film with good adherence to the skin | Forms a distinct very robust film with good adherence to the skin | Forms a distinct very robust film with good adherence to the skin | Forms a discrete very robust film with good adherence to the skin |
| Wear time or exposed film. | 48 hours before any cracking. Main bulk of the film last for a further day. | 48 hours before any cracking. Main bulk of the film last for a further day. | 72 hours before any cracking. Main bulk of the film last for a further 2 days. | 72 hours before any cracking. Main bulk of the film last for a further 2 days. |
| Adhesion of dressing to film/skin | Good | Good | Good | Good |

| Components | Example 26 | Example 27 | Example 28 | Example 29 |
|---|---|---|---|---|
| Avalure AC 118 | 44% | 44% | 44% | 44% |
| Avulure UR 425 | 44% | 44% | 44% | 44% |
| Water | 7.7% | 7.7% | 7.7% | 7.7% |
| Sodium Chloride | 0.3% | 0.45% | 0.6% | 0.9% |
| Glycerol | 4% | 4% | 4% | 4% |
| Sterilised? | yes | yes | yes | yes |
| Format before gamma | Liquid | Thick liquid | Cream | Semi solid emulsion |
| Format after gamma | Liquid | Thick liquid | Cream | Semi solid emulsion |
| Drying Time | 3 mins | 3 mins | 3 mins | 3.5 mins |
| Film format | Forms a distinct very robust film with good adherence to the skin | Forms a distinct very robust film with good adherence to the skin | Forms a distinct very robust film with good adherence to the skin | Forms a discrete very robust film with good adherence to the skin |
| Wear time or exposed film. | 72 hours before any cracking. Main bulk of the film last for a further day. | 72 hours before any cracking. Main bulk of the film last for a further day. | 72 hours before any cracking. Main bulk of the film last for a further 2 days. | 72 hours before any cracking. Main bulk of the film last for a further 3 days. |
| Adhesion of dressing to film/skin | Good | Good | Good | Good |

It is of course to be understood that the invention is not intended to be restricted to the details of the above embodiments which are described by way of example only.

The invention claimed is:

1. A gamma radiation sterilized sterile liquid film forming composition for application to mammalian skin or a breach in the skin comprising 10-90% w/w at least one polyurethane based polymer, 25-50% w/w of at least one acrylate based polymer and a solvent comprising water,
    wherein the composition is in liquid form upon application, and dries in situ to form a discrete uniform film on application to mammalian skin or a breach in the skin.

2. A film forming composition according to claim 1, wherein, in use, said composition dries in situ in less than 10 minutes to form a film on mammalian skin.

3. A film forming composition according to claim 1, wherein said polyurethane based polymer is in the form of an emulsion, a fluid suspension, a solution or any combination thereof.

4. A film forming composition according to claim 1, wherein said polyurethane based polymer is selected from the following either alone or in combination: polyurethane, polyetherpolyurethane, polyureapolyurethane, copolymers of polyurethane, polyurethane/silicone copolymers, polyurethane/acrylic copolymers, polyurethane adhesives, polyurethane derivatives, polyurethane elastomers, polyurethane prepolymers, polyurethane hydrogels.

5. A film forming composition according to claim 1, wherein said polyurethane-based polymer constitutes from 50% to 75% w/w of the total composition.

6. A film forming composition according to claim 1, wherein said acrylate based polymer is in the form of an emulsion, a fluid suspension, a solution or any combination thereof.

7. A film forming composition according to claim 1, wherein said acrylate based polymer is selected from the following either alone or in combination: polyacrylic acid, carbomer, carboxyvinyl polymer, carboxypolymethylene polymer, polyacrylate elastomers, polyacrylates, polyacrylate copolymer, polyacrylate crosspolymers, acrylates/alkyl acrylate crosspolymer, AMP-acrylates/Allyl Methacrylate Copolymer, acrylates/acrylamide copolymer, acrylic acid/alkyl methacrylate copolymer, silicone/acrylates copolymer, acrylates/polyurethane copolymer.

8. A film forming composition according to claim 1, wherein the composition further comprises any of the following either alone or in combination: viscosity enhancing compounds; polyols; solvents; volatile solvents; antimicrobials; preservatives; waterproofing agents; growth factors; healing agents; surfactants; moisturisers; herbal extracts; amino acids; pH altering compounds; cleansers; and haemostats.

9. A film forming composition according to claim 8, wherein said viscosity enhancing compound is a viscosity enhancing salt.

10. A film forming composition according to claim 9, wherein said viscosity enhancing salt is sodium chloride.

11. A film forming composition according to claim 8, wherein said antimicrobial is selected from one or more of silver salts, silver complexes, antibiotics, zinc, copper, chlorhexidine, and benzalkonium halides.

12. A film forming composition according to claim 1, wherein said composition is visible when applied to mammalian skin or a breach in the skin.

13. A film forming composition according to claim 1 wherein said composition is provided with an applicator operable to facilitate the application of said composition to mammalian skin or a breach in the skin.

14. A film forming composition according to claim 1, wherein said composition is in the form of a spray.

15. A skin wipe comprising a film forming composition according to claim 1 adsorbed onto a fibrous material.

16. A skin wipe according to claim 15, wherein said fibrous material is a cellulose material.

17. A skin protector comprising a film forming composition according to claim 1.

18. A wound dressing comprising a film forming composition according to claim 1.

19. A polymeric protective film obtainable by applying to mammalian skin or a breach in the skin a film forming composition according to claim 1.

20. A method of treating skin with a skin protector comprising the steps of:
providing a polyurethane based polymer and an acrylate based polymer;
mixing 10-90% w/w said polyurethane based polymer and 25-50% w/w of said acrylate based polymer and a solvent comprising water to form a liquid skin protector;
irradiating the liquid skin protector with gamma radiation; and
applying a therapeutically effective amount of said gamma irradiated, liquid skin protector to mammalian skin, wherein the gamma irradiated, liquid skin protector dries in situ and forms a discrete uniform film on application to mammalian skin.

21. A method of treating a wound with a wound dressing comprising the steps of:
providing a polyurethane based polymer and an acrylate based polymer;
mixing 10-90% w/w said polyurethane based polymer and 25-50% w/w of said acrylate based polymer and a solvent comprising water to form a liquid wound dressing;
irradiating the liquid wound dressing with gamma radiation; and
applying a therapeutically effective amount of said gamma irradiated, liquid wound dressing to mammalian skin or a breach in said skin, wherein the gamma irradiated, liquid wound dressing dries in situ and forms a discrete uniform film on application to mammalian skin or a breach in said skin.

22. A method for the preparation of a radiation sterilized sterile liquid film forming composition, comprising the steps of:
mixing together 10-90% w/w of a polyurethane based polymer and 25-50% w/w of an acrylate based polymer and a solvent comprising water to form a liquid film forming composition, and
irradiating the liquid film forming composition using gamma radiation,
wherein the irradiated, liquid film forming composition dries in situ and forms a discrete uniform film on application to mammalian skin or a breach in the skin.

23. A gamma radiation sterilized sterile liquid film forming composition for application to mammalian skin or a breach in the skin, obtainable by
mixing together 10-90% w/w of a polyurethane based polymer and 25-50% w/w of an acrylate based polymer and a solvent comprising water to form a liquid film forming composition, and
irradiating the resulting liquid film forming composition using gamma radiation,
wherein the gamma irradiated, liquid film forming composition dries in situ to form a discrete uniform film on application to mammalian skin or a breach in the skin.

* * * * *